United States Patent
Garcia-Bengochea et al.

(10) Patent No.: US 8,403,963 B2
(45) Date of Patent: Mar. 26, 2013

(54) METHOD AND APPARATUS FOR SPINAL FIXATION USING MINIMALLY INVASIVE SURGICAL TECHNIQUES

(76) Inventors: Javier Garcia-Bengochea, Jacksonville, FL (US); Andrew F. Cannestra, Jacksonville, FL (US)

( * ) Notice: Subject to any disclaimer, the term of this patent is extended or adjusted under 35 U.S.C. 154(b) by 330 days.

(21) Appl. No.: 12/930,989

(22) Filed: Jan. 21, 2011

(65) Prior Publication Data

US 2011/0184473 A1 Jul. 28, 2011

Related U.S. Application Data

(60) Provisional application No. 61/336,524, filed on Jan. 22, 2010.

(51) Int. Cl.
*A61B 17/88* (2006.01)
(52) U.S. Cl. .......................... 606/279; 606/246; 606/264
(58) Field of Classification Search .......... 606/246–279, 606/914, 86 A
See application file for complete search history.

(56) References Cited

U.S. PATENT DOCUMENTS

| | | | |
|---|---|---|---|
| 6,221,077 B1 | 4/2001 | Riner et al. |
| 6,423,071 B1 | 7/2002 | Lawson |
| 6,821,277 B2 | 11/2004 | Teitelbaum |
| 7,188,626 B2 | 3/2007 | Foley et al. |
| 2005/0033289 A1 | 2/2005 | Warren et al. |
| 2008/0015582 A1 | 1/2008 | DiPoto et al. |
| 2008/0234738 A1 | 9/2008 | Zylber et al. |
| 2009/0171392 A1 | 7/2009 | Garcia-Bengochea et al. |

*Primary Examiner* — Andrew Yang
(74) *Attorney, Agent, or Firm* — Thomas C. Saitta

(57) ABSTRACT

An improved method and guide wire assembly used in a system, set of instrumentation and method comprising the combination and use of plural pedicle screws, a rod for connecting pedicle screws in a relatively rigid manner, and instrumentation to optimize insertion of the rod into the pedicle screws, the assembly having a guide wire and instrumentation to grasp a medial portion of the guide wire to pull the medial portion through all the pedicle screws and connecting the loop to the end of a fixation rod, whereby one end of the guide wire is mounted to a pedicle screw, all the screws are implanted into the vertebrae, and the rod subsequently guided into the pedicle screws by pulling the guide wire loop back through the pedicle screws, all using minimally invasive surgical incisions.

12 Claims, 6 Drawing Sheets

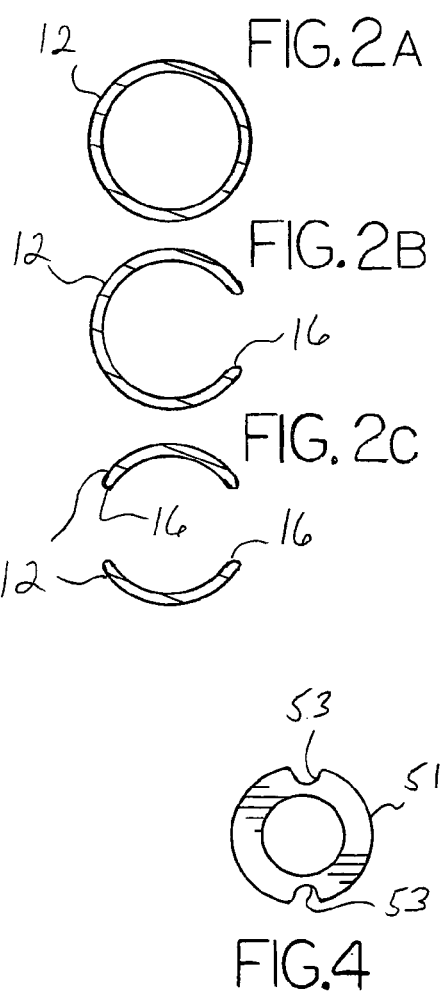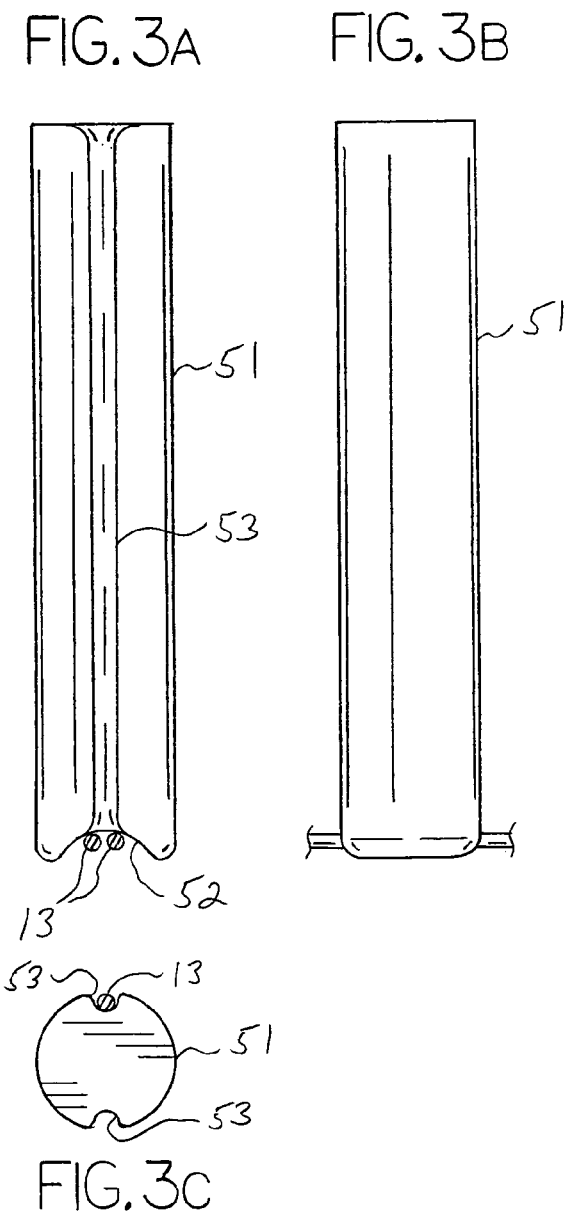

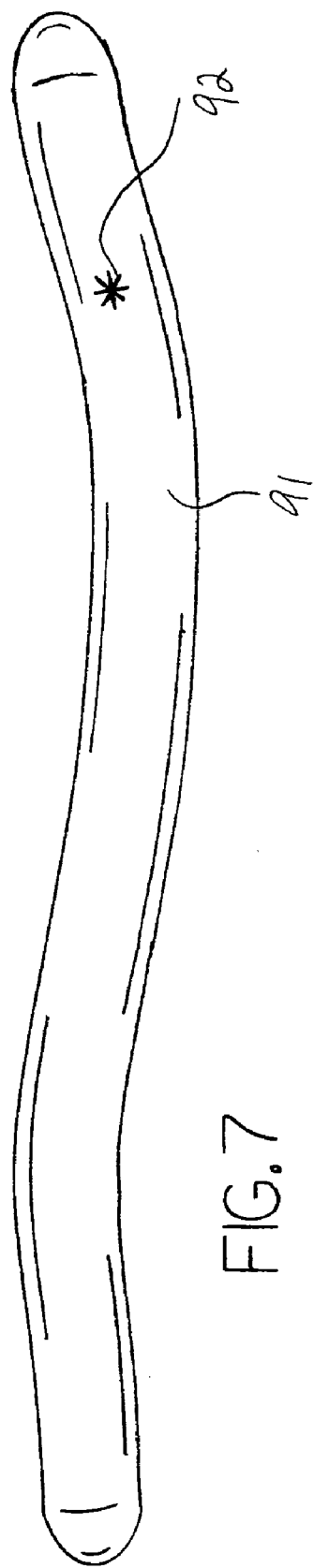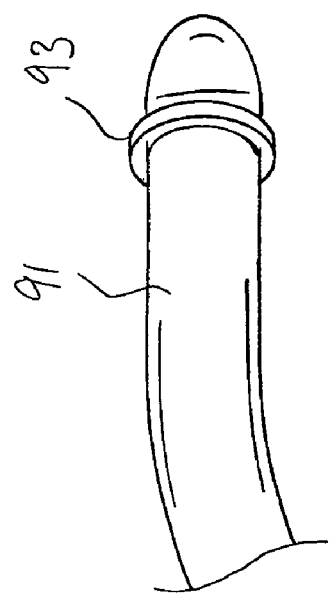

METHOD AND APPARATUS FOR SPINAL FIXATION USING MINIMALLY INVASIVE SURGICAL TECHNIQUES

This application claims the benefit of U.S. Provisional Patent Application Ser. No. 61/336,524, filed Jan. 22, 2010.

BACKGROUND OF THE INVENTION

This invention relates generally to the field of systems, instrumentation and methodology for the fixation or fusing of vertebrae relative to each other, and more particularly relates to such systems, instrumentation and methodology that utilize pedicle screws affixed to vertebral pedicles and one or more rods that rigidly connect the pedicle screws of plural vertebrae. Even more particularly, the invention relates to such systems, instrumentation and methodology that utilize a guide wire inserted through the pedicle screws as a means to guide and locate a fixation or stabilization rod through the pedicle screws.

Traditional surgical techniques for affixing rods to vertebrae entail the creation of relatively long incisions to provide access to the vertebrae. Large bands of back muscles are stripped and pulled free from the spine (i.e., retracted) to provide access to the vertebrae. Newer techniques utilize single or multiple short or stab percutaneous incisions at chosen locations rather than a single long incision, with tubular cannulas being inserted to provide access pathways to the vertebrae. Such techniques are often referred to as minimally invasive surgery (MIS). The MIS techniques are preferable with regard to recovery time, since muscle retraction, muscle stripping and the like are minimized or obviated.

The relevant MIS technique for stabilizing the spine involves the insertion of pedicle screws into the vertebral pedicles. A pedicle is the strong, cylindrical, anatomic bridge between the dorsal spine elements and the vertebral body, and is comprised of a strong shell of cortical bone and a core of cancellous bone. Each vertebra has two pedicles and these provide a sturdy base to securely receive the threaded shaft of a pedicle screw. The pedicle screw may be a rigid member, but most preferably comprises a slotted, rod-receiving head mounted in a swiveling or rotating manner to a threaded shaft, such as for example by the use of a ball and socket-type connection. Such screw structures provide greater latitude in connecting the fixation rod and are well known in the art. Spinal fixation or fusion is accomplished by inserting pedicle screws into multiple vertebrae and connecting the screws to each other with a rigid rod secured to the receiving heads of the screws, thereby stabilizing the vertebrae.

In one MIS technique, a relatively small incision is made through the back to expose the vertebrae and pedicle screws are affixed to the pedicles of adjoining vertebrae using cannulated or tubular sleeve extenders. The rod is then transversely passed down through the sleeve extenders, laid into the slots of the receiving heads of the screws and secured using the set screws of the receiving heads, typically externally threaded members received by the internally threaded receiving heads. The rod joins all the pedicle screws and therefore the vertebrae in a fixed and rigid manner. Because the rod is inserted in a non-axial direction, there is still excessive damage to the muscles and other tissue because a slit must be provided, and recovery time is lengthened and healing pain is increased.

In another MIS technique, one or more short incisions or stab incisions are utilized for insertion of the pedicle screws. An example of this system is described in U.S. Pat. No. 7,188,626, issued Mar. 13, 2007 to Foley et al., the disclosure of which is incorporated herein by reference. In this technique, the sleeve extenders are joined and secured, and a swinging rod inserter is connected to this assembly of extenders. The rod inserter delivers a rod through the skin and tissue in an arced pathway and into the receiving heads of the pedicle screws. A problem with this system is that the pedicle screws are often not aligned in a linear manner and may also vary in height. The more out of alignment the receiving heads are, the more difficulty there is in using the swinging rod inserter to deliver the rod. Another problem with this system is that the rod is not restrained or guided along the insertion path in and between the pedicle screws.

In still another MIS technique, a guide wire, suture, cable or similar flexible member is first passed down through a sleeve extender and then through the pedicle screws. The leading end of the guide wire is then passed out through the last sleeve extender or through another incision. Examples of this technique are described in U.S. Pat. No. 6,821,277, issued Nov. 23, 2004 to Teitelbaum, and in U.S. Patent Application Publication No. 2008/0015582, published Jan. 17, 2008 in the name of DiPoto et al., the disclosure of both being incorporated herein by reference.

In our pending patent application Ser. No. 12/315,546, the disclosure of which is incorporated herein by reference, an improved MIS system is provided, the system having a guide wire, suture, cable or similar flexible member as part of a spinal fixation MIS procedure, the guide wire being connected to a collar member for ready mounting onto a pedicle screw. With the guide wire affixed to a first pedicle screw, the free end of the guide wire is passed through the remaining pedicle screws and out of the patient. A fixation rod is then connected to the free end of the guide wire and pulled into position in the pedicle screws.

It is an object of this invention to provide an improved MIS apparatus and methodology for insertion and positioning of the fixation rod in the pedicle screws. It is an object to provide a methodology whereby an interior portion of the guide wire rather than a free end is pulled through the pedicle screws, such that a guide wire loop is presented for connection to the fixation rod. It is an object to provide an apparatus and methodology whereby a malleable template rod is first inserted into the pedicle screws, the malleable rod then being bent to identify the proper configuration for alignment with the pedicle screws, the properly configured malleable rod then being removed from the patient, the permanent fixation rod then being bent to conform to the configuration of the malleable rod prior to insertion and fixation to the pedicle screws. It is an object to provide an apparatus whereby the proper length for the permanent fixation rod is determined by measurements taken of the guide wire or the malleable rod. It is an object to provide an apparatus and methodology enabling alignment of the pedicle screws by positioning the fixation rod in the pedicle screws, manipulating the rod and/or affixing the rod to one of the pedicle screws and then manipulating the rod to properly align an adjacent pedicle screw, affixing the rod to this pedicle screw, and continuing the process.

SUMMARY OF THE INVENTION

In a system, set of instrumentation and method comprising the combination and use of plural pedicle screws affixed to the pedicles of vertebrae, one or more rods for connecting pedicle screws to each other in a relatively rigid manner, and instrumentation means to direct insertion of the rod into the pedicle screws, such means comprising a guide wire and instrumentation to position the guide wire in and between the receiving heads of the pedicle screws, whereby the guide wire is positioned in and between the receiving heads of the pedicle screws implanted into the vertebrae, and the rod subsequently connected to the guide wire and inserted through the skin and tissue in a generally axial direction and guided into the receiving heads of the pedicle screws by the guide wire, all using minimally invasive surgical incisions, the improvement comprising providing means to connect one end of the guide wire to an outermost pedicle screw, providing means to grasp the guide wire at a medial portion and pull the guide wire through all pedicle screws and out of the body through an MIS incision, such that the free end of the guide wire is not pulled into the body and a looped portion of the guide wire extends outside of the body, attaching a fixation rod to the looped portion of the guide wire, and pulling the free end of the guide wire in order to draw the fixation rod through the incision and into the pedicle screws. The rod is then secured to the pedicle screws using setscrew-type members that mate with the receiving heads of the pedicle screws.

In a further or alternate embodiment, the invention comprises an MIS apparatus and methodology whereby a malleable template rod is first inserted into the pedicle screws, the malleable rod then being bent to identify the proper configuration for alignment with the pedicle screws, the properly configured malleable rod then being removed from the patient, the permanent fixation rod then being bent to conform to the configuration of the malleable rod prior to insertion and fixation to the pedicle screws. In a further or alternate embodiment, the invention comprises an MIS apparatus and methodology whereby the proper length for the permanent fixation rod is determined by measurements taken of the guide wire or the malleable rod. In a further or alternate embodiment, the invention comprises an MIS apparatus and methodology enabling alignment of the pedicle screws by positioning the fixation rod in the pedicle screws, manipulating the rod and/or affixing the rod to one of the pedicle screws and then manipulating the rod to properly align an adjacent pedicle screw, affixing the rod to this pedicle screw, and continuing the process.

BRIEF DESCRIPTION OF THE DRAWINGS

FIGS. 2A-C are cross-sectional views of different sleeve extenders.

FIGS. 3A-C are views of the piston member.

FIG. 4 is an end view of an alternative embodiment piston member.

FIG. 7 is a view of a malleable template rod having been configured to match the alignment of the pedicle screws and showing the presence of a measurement mark.

FIG. 8 is a view of a template rod showing the presence of a marking collar.

DETAILED DESCRIPTION OF THE INVENTION

In general, the invention is an apparatus and methodology comprising a guide wire having a mounting collar or other means of fixation to a pedicle screw that is used with a system, set of instrumentation and method comprising the combination and use of plural pedicle screws implanted into vertebrae, at least one fixation rod for connecting and bridging the pedicle screws and vertebrae in a relatively rigid manner, and instrumentation means to optimize insertion of the rod into the pedicle screws, such means comprising a guide wire and instrumentation to position the guide wire in the pedicle screws, whereby the screws are implanted into the vertebrae, the guide wire positioned in the screws and the rod subsequently guided into the pedicle screws along the guide wire, all using minimally invasive surgical (MIS) incisions.

Figure 1:
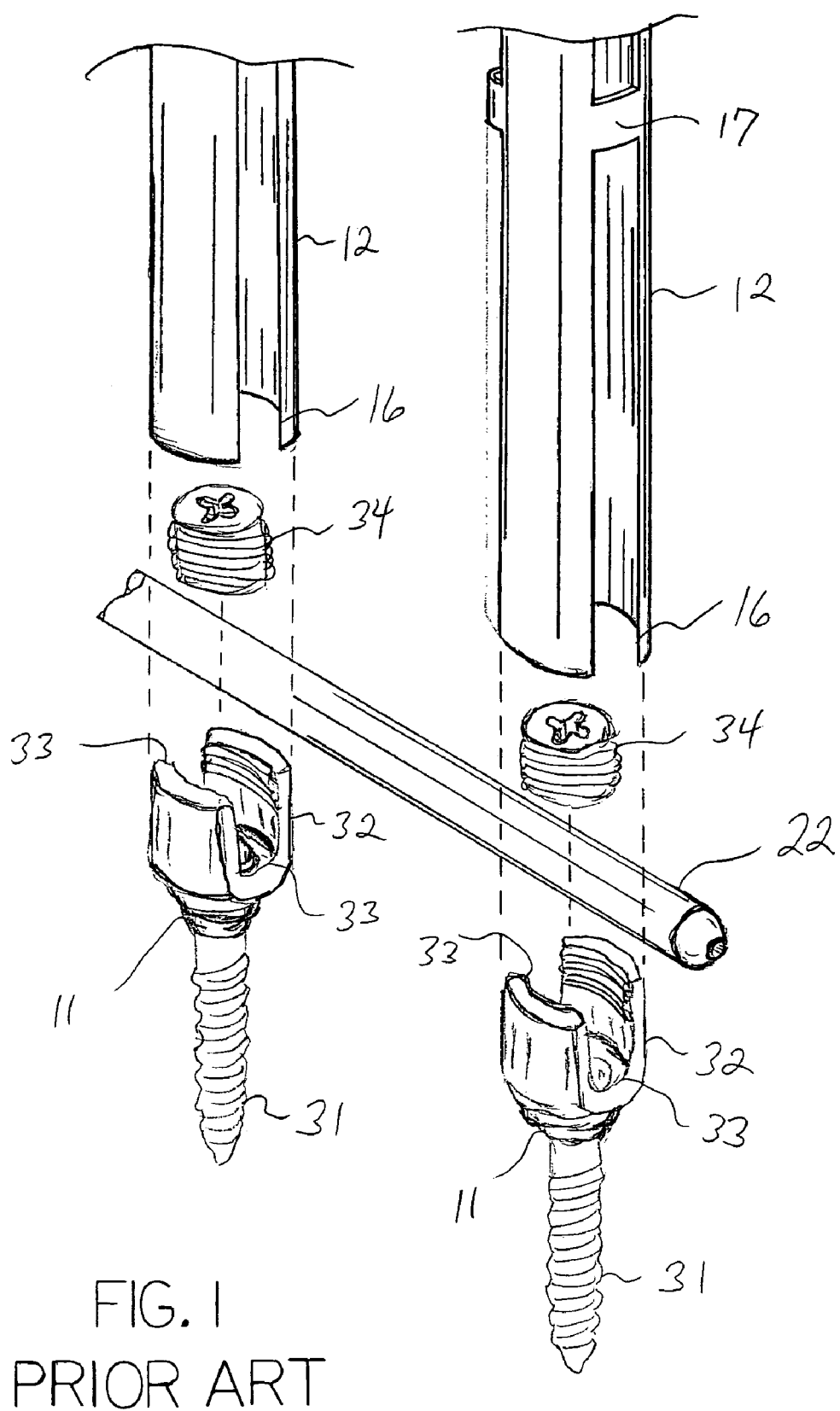
FIG. 1 is an exploded view showing representative prior art pedicle screws, sleeve extenders and a fixation rod.

Pedicle fixation in MIS is accomplished by creating a single incision or multiple, relatively short, percutaneous incisions, such incisions for example being less than 10 millimeters in length for stab incisions or from about 2 to 4 centimeters in length for standard scalpel incisions, as opposed to creating a long incision, often referred to as an open incision, which may cover 10 or more centimeters. The MIS incisions allow for pedicle screws 11 to be inserted into each desired vertebral pedicle by cutting or making one or multiple short incisions, temporarily positioning tubular distraction cannulas to provide access through the tissue to each of the vertebral pedicles, drilling into the vertebra and inserting a threaded pedicle screw 11 using a drive tool and/or a screw sleeve extender or tower 12. Most preferably, the pedicle screws 11 utilized in this invention comprise a threaded shaft 31 extending from a rod-receiving head 32, the head 32 having opposing slots 33, and rod-securing members 34, such as an externally threaded set screw mating with internal threads of the rod-receiving head 32, wherein the head 32 is mounted to the shaft 31 in a manner that allows the head 32 to swivel and rotate. With this structure, the head slots 33 can be more easily aligned to better receive the fixation rod 22 after the screws 11 have been implanted into the vertebrae. The sleeve extenders 12 are temporarily connected to the pedicle screws 11 and are removed once the fixation rod 22 has been secured to the pedicle screws 11. The sleeve extenders 12 are tubular members preferably having opposing longitudinal slots 16 at least at their distal ends. Most preferably, the slots 16 extend over the majority of the length of the sleeve extenders 12 with only short bridging sections 17 provided, whereby for example the profile of the sleeve extender 12 is that of an "H" when viewed laterally through aligned slots 16. Such devices, instrumentation and techniques are known in the art, and an illustration is provided as FIG. 1 herein.

A guide wire, cable, suture or similar flexible member 13 is provided, preferably composed of braided stainless steel or titanium, the guide wire 13 being of sufficient length to extend through all of the implanted pedicle screws 11 and then out through the skin of the patient. One end of the guide wire 13, to be referred to as the affixed end, is attached to a collar, ring or similar wire fixation member 35 that receives the shaft 31 of the pedicle screw 11 or is otherwise connected to the pedicle screw 11, such that the affixed end of the guide wire 13 is positioned adjacent the head 32 of the first or distal of the implanted pedicle screws 11 and is preferably held in place between the head 32 and the vertebra. The wire affixation member 35, which may be annular or C-shaped for example, is placed onto the shaft 31 prior to implantation of the pedicle screw 11. The guide wire 13 may be permanently affixed to the wire affixation member 35 or may be joined in a releasable manner, where for example the affixed end of the wire 13 is provided with a hook member that is temporarily secured to an eyelet on the ring member 35.

An elongated piston or plunger member 51 is provided for each sleeve extender 12, the piston members 51 being coaxially insertable into the sleeve extenders 12. The piston members 51 are axially and rotationally movable when inserted into the sleeve extenders 12. The base of the piston member 51 is preferably provided with a distal recess 52, as shown in FIG. 3A, the distal recess 52 serving to properly position the guide wire 13 and the fixation rod 22. At least one of the piston members 51 may also be provided with one or more longitudinal recesses or channels 53, sized to receive the guide wire 13, as shown in FIGS. 3A and 3C. The piston members 51 may also be tubular, as shown in FIG. 4. Means for securing the piston members 51 within the sleeve extenders 12 at a desired position may be provided, such as clip members or the like that fasten to the sleeve extenders 12.

Figure 5A:
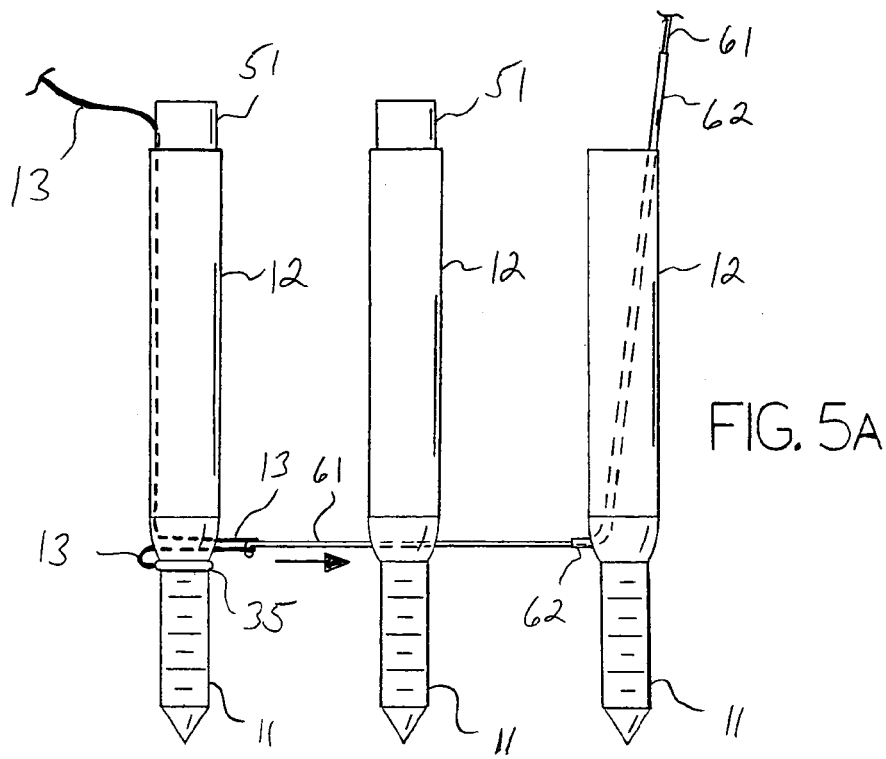
FIGS. 5A-D are successive views illustrating an embodiment of the rod insertion and positioning methodology.
Figure 5B:
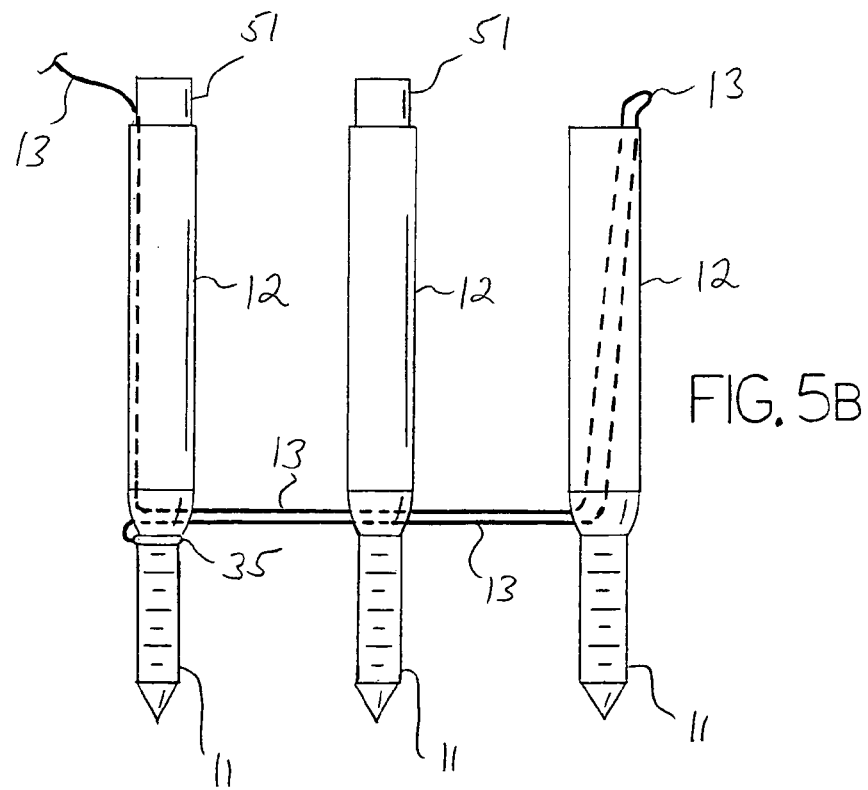

With the piston members 51 in place within the sleeve extenders 12 as shown in FIG. 5A, a medial portion of the guide wire 13 is hooked or grasped using grasping means, such as an extendible wire 61 sheathed within a sleeve 62, and the medial portion of the guide wire 13, now in a looped configuration, is then pulled through all the pedicle slots 33 beneath the piston members 51 and out of the last sleeve extender 12, which at this point contains no piston member 51. Alternatively, an additional incision may be created beyond the last sleeve extender 12 and the looped guide wire 13 may be pulled through this incision.

The guide wire 13 may be utilized a measurement device to determine the proper length of the fixation rod 22. This may be accomplished by providing visible markings on the guide wire 13, spaced for example every half centimeter, or by utilizing a known length of guide wire 13 and measuring the length of wire extending through and from the last sleeve extender 12, then performing the required calculations to determine the length of wire extending between the pedicle screws 11. Use of a guide wire as a measurement device is also appropriate in methodologies wherein the free end of the guide wire is pulled through the patient rather than the looped portion as described herein.

Figure 5C:
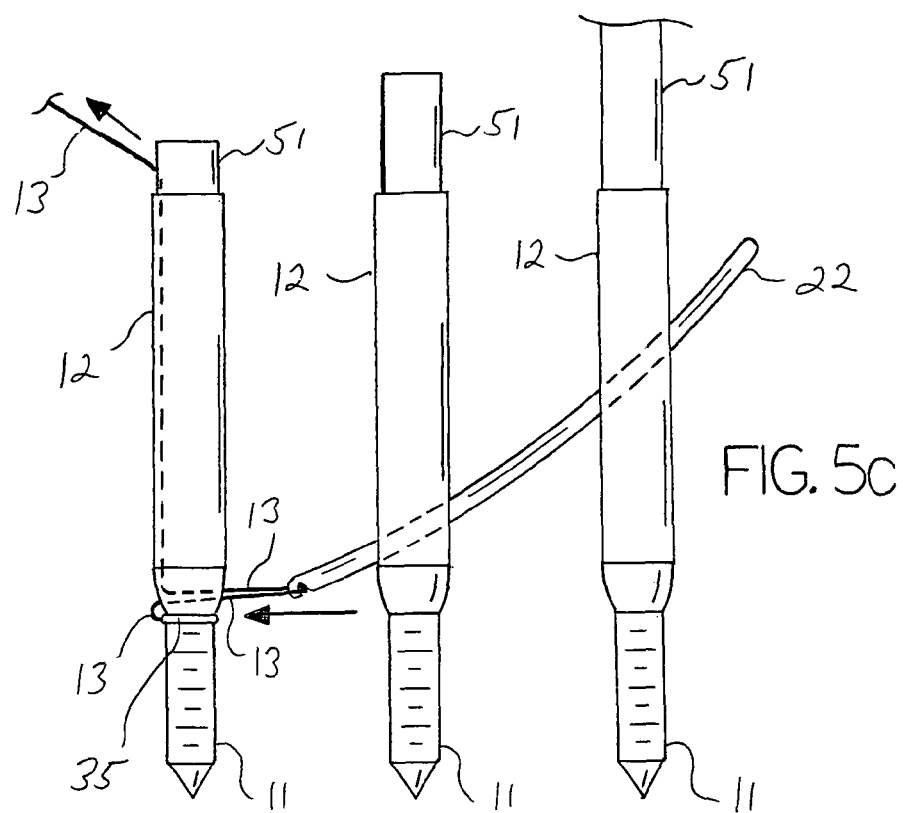
Figure 5D:
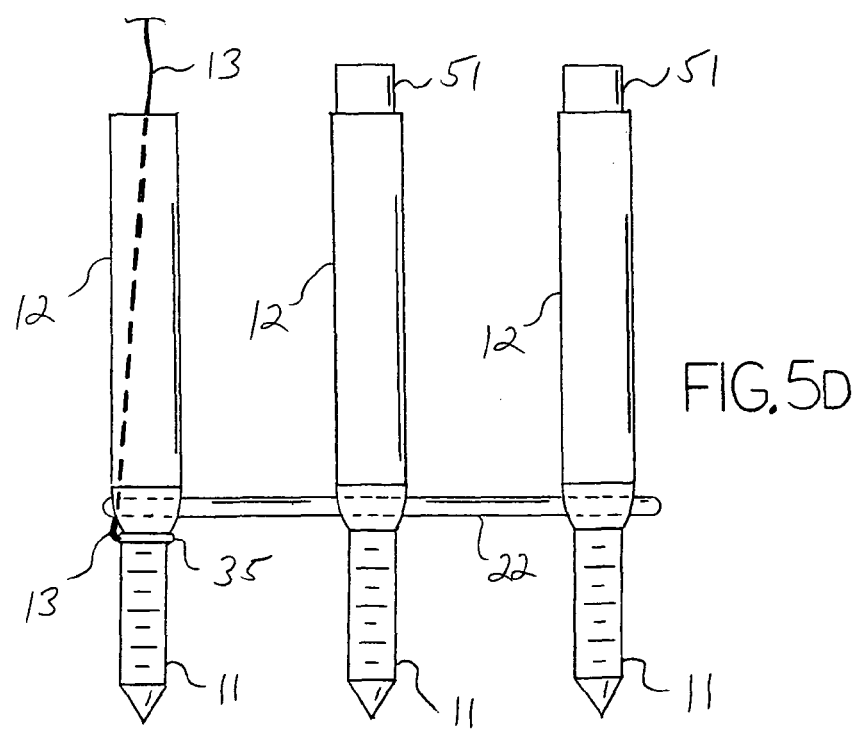

A fixation rod 22 is then connected to the looped guide wire 13 in suitable manner, such as by providing the end of the fixation rod 22 with a hooked portion or other mechanical construct or connector to receive the looped guide wire 13 in sliding manner, and the free end of the guide wire 13 is pulled so as to draw the fixation rod 22 into the pedicle screws 11. The piston members 51 maintain the guide wire 13 and fixation rod 22 in a lowermost or distal position as the rod 22 is positioned within the screws 11, as shown in FIGS. 5C and 5D, preventing damage to body tissues during the rod insertion process. With the fixation rod 22 in proper position, the excess guide wire 13 is then severed and removed.

Figure 6:
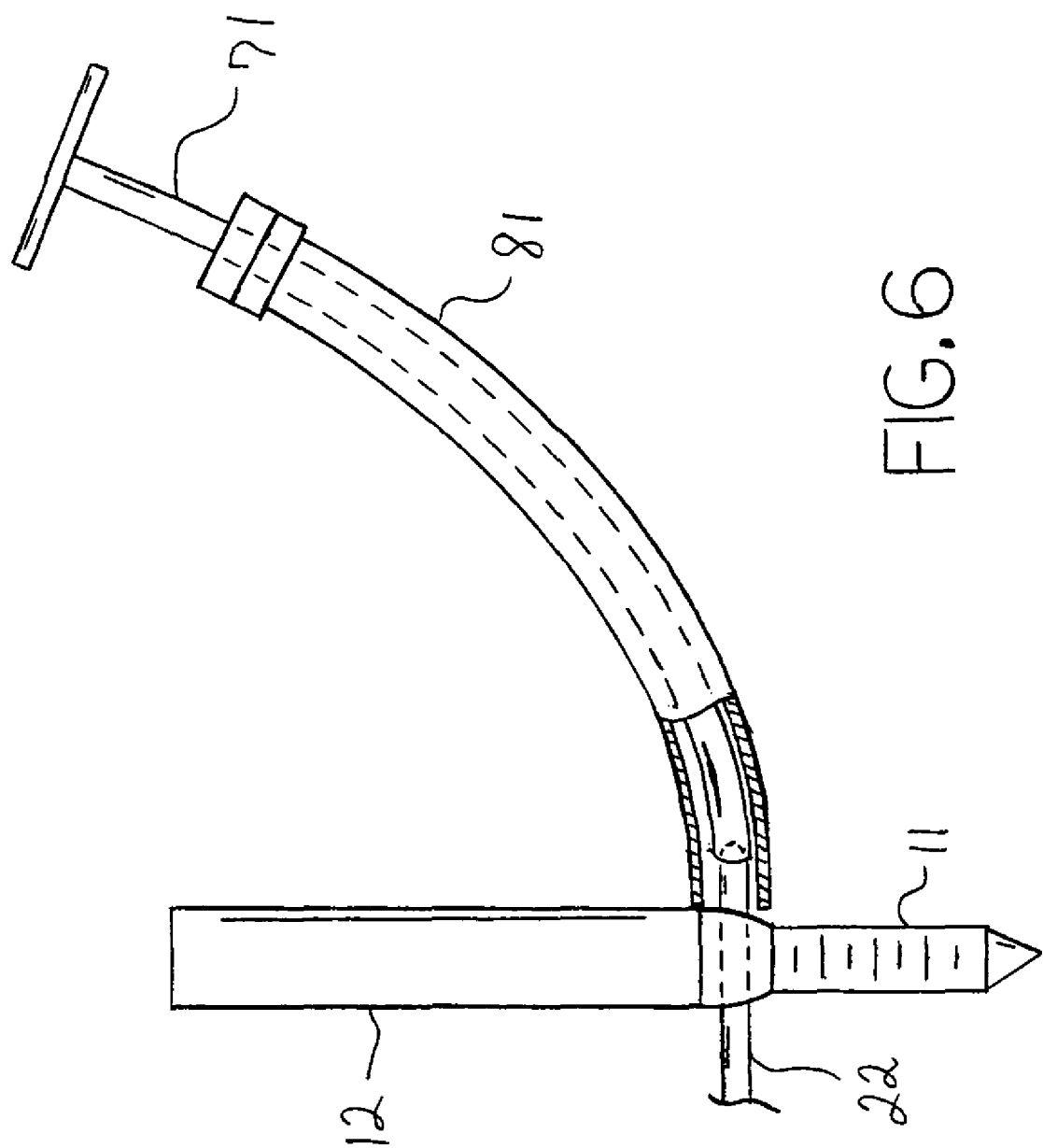
FIG. 6 is a view of a rod directing tool and a compression tool positioned at the proximal end of the fixation rod.

In an additional or alternative embodiment, as shown in FIG. 6, a rod directing tool 71 may be provided. Rod directing tool 71 is a means for pushing or controlling the position of the fixation rod 22 at its proximal end, and is an elongated member, preferably curved, having a proximal handle or gripping member. Means for temporarily interlocking or connecting the rod directing tool 71 to the proximal end of the rod 22 are provided, such as for example a socket or mechanically operable clasping fingers or prongs. Alternatively, the end configuration of the rod 22 and the end configuration of the rod directing tool 71 may be structured to match or mate. With this rod directing tool 71, the fixation rod 22 is pulled in the distal direction by the guide wire 13 while simultaneously being pushed at the proximal end of the rod 22. Use of a rod directing tool is also appropriate in methodologies wherein the free end of the guide wire is pulled through the patient rather than the looped portion as described herein.

In many instances the relative orientation and alignment of the pedicle screws 11 need to be adjusted prior to final fixation of the rod 22 in order to properly position the vertebrae. In one methodology, a compression tool 81 is provided, the compression tool 81 comprising for example an elongated sleeve member that slides over the rod directing tool 71 and the proximal end of the fixation rod 22 to abut the side of the pedicle screw 11 and/or the base of the sleeve extender 12. The compression tool 81 is constructed to be flexible so as to be able to bend to conform to the bend in the rod directing tool 71, yet be non-compressible in the axial direction such that force may be applied against the pedicle screw 11. In this manner the pedicle screw 11 can be forced in the axial direction of the fixation rod 22 to achieve proper alignment, the pedicle screw 11 then being fastened to the rod 22 prior to retraction of the compression tool. The compression tool 81 may also serve as a measuring instrument. Use of a compression tool is also appropriate in methodologies wherein the free end of the guide wire is pulled through the patient rather than the looped portion as described herein.

For multiple vertebrae, realignment may be accomplished for example by inserting the rod 22 through the pedicle screws 11, locking down the distal end of the rod 22 in the distal pedicle screw 11, then advancing the compression tool 81 against the proximal pedicle screw 11 to properly position it relative to the distal pedicle screw 11, then locking down proximal pedicle screw 11. For instances with three pedicle screws 11, the rod 22 is inserted and locked onto the intermediate pedicle screw 11, the compression tool 81 is advanced against the proximal screw 11 to properly position it relative to the intermediate pedicle screw 11, then the rod 22 is locked to the proximal pedicle screw 11. Next, the compression tool 81 is used to move the fixed combination of the intermediate and proximal pedicle screws 11 relative to the distal pedicle screw 11, which is then locked to the rod 22.

In an alternative or additional embodiment, the fixation rod 22 may be inserted into position within the pedicle screws 11, the rod 22 then being grabbed or otherwise controlled at both ends using suitable instruments such that the rod 22 is used as a leveraging tool to provide compression, distraction, reduction or rotation of a pedicle screw 11 as required. This methodology is also appropriate in techniques wherein the free end of the guide wire is pulled through the patient rather than the looped portion as described herein.

In an alternative or additional embodiment, the methodology may include the use of a malleable template rod, composed of aluminum or like relatively-soft material. This template rod 91 is first inserted into pedicle screws 11 in the same manner as described above relative to the fixation rod 22. Once in place within the pedicle screws 11, the piston members 51 are utilized to force the template rod 91 into a fully seated position for each pedicle screw 11, thereby bending the malleable template rod 91 and resulting in a rod configuration that properly matches the orientation of the pedicle screws 11, as seen for example in FIG. 7. The template rod 91 is then removed and the fixation rod 22 is bent into a matching configuration, such that upon insertion of the fixation rod 22 it will precisely correspond to the orientation of the pedicle screws 11. Use of a malleable template rod is also appropriate in methodologies wherein the free end of the guide wire is pulled through the patient rather than the looped portion as described herein.

The malleable template rod 91 may also be utilized to provide a measurement as to the required length of the fixation rod 22. One technique is to insert a piston member 51 or other marking tool into the proximal sleeve extender 12 when the template rod 91 is in proper position, such that a mark or impression 92 is visible on the template rod 91 when it is removed. An alternate technique is to advance a marking collar 93 down the rod directing tool 71 and over the template rod 91 to abut the proximal pedicle screw 11, then locking, either mechanically or using friction, the collar 93 onto the template rod 91 to indicate its desired length, as shown in FIG. 8.

It is understood that equivalents and substitutions to certain elements and steps set forth above may be obvious to those of ordinary skill in the art, and therefore the true scope and definition of the invention is to be as set forth in the following claims. The illustrations and examples given herein are not meant to be limiting.

We claim:

1. A minimally invasive surgery method of spinal fixation comprising the steps of:
    creating one or more short percutaneous incisions in the back of a patient;
    inserting pedicle screws through said incisions and affixing said pedicle screws into multiple vertebrae, each of said pedicle screws comprising a rod-receiving head;
    affixing a guide wire to one of said pedicle screws, said guide wire thereby having an attached end and a free end;
    passing a medial portion of said guide wire through said pedicle screws, whereby said free end is not pulled through said patient and remains disposed outside of said patient;
    connecting an end of a fixation rod to said medial portion of said guide wire;
    pulling said free end of said guide wire such that said fixation rod is pulled into said rod-receiving heads of said pedicle screws;
    securing said fixation rod to said pedicle screws; and
    cutting said guide wire.

2. The method of claim 1, further comprising the step of:
    connecting towers to each of said pedicle screws, whereby said step of passing a medial portion of said guide wire through said pedicle screws comprises inserting a grasping tool through one or more of said towers and grasping said medial portion of said guide wire.

3. The method of claim 2, further comprising the steps of:
    positioning one or more piston members in said towers;
    using said piston members to control the location of said guide wire during said step of passing a medial portion of said guide wire through said pedicle screws; and
    using said piston members to control the location of said fixation rod during said step of pulling said fixation rod into said rod-receiving heads of said pedicle screws and said step of securing said fixation rod to said pedicle screws.

4. The method of claim 1, further comprising the steps of:
    connecting a rod directing tool to the end of the fixation rod not connected to said medial portion of said guide wire; and
    pushing said fixation rod with said rod directing tool while performing said step of pulling said free end of said guide wire such that said fixation rod is pulled into said rod-receiving heads of said pedicle screws.

5. The method of claim 2, wherein said step of connecting a fixation rod to said medial portion of said guide wire comprises pulling said guide wire medial portion out of one of said towers.

6. The method of claim 2, wherein said step of connecting a fixation rod to said medial portion of said guide wire comprises pulling said guide wire medial portion out of one of said incisions not associated with any of said towers.

7. The method of claim 1, further comprising the steps of:
    connecting a malleable template rod to said guide wire medial portion and pulling said template rod into said rod-receiving heads of said pedicle screws;
    bending said template rod to conform to said pedicle screws;
    withdrawing said template rod and said guide wire medial portion; and
    bending said fixation rod to conform to the configuration of said template rod prior to pulling said fixation rod into said rod-receiving heads of said pedicle screws.

8. The method of claim 2, further comprising the steps of:
    connecting a template rod to said guide wire medial portion and pulling said template rod into said rod-receiving heads of said pedicle screws;
    marking said template rod through one of said towers;
    withdrawing said template rod and said guide wire medial portion;
    utilizing said marking of said template rod to determine the proper length of said fixation rod, and cutting said fixation rod.

9. The method of claim 1, further comprising the steps of:
    providing distance indicia on said guide wire, utilizing said indicia to determine the proper length of said fixation rod, and cutting said fixation rod.

10. The method of claim 1, further comprising the steps of:
    connecting a template rod to said guide wire medial portion and pulling said template rod into said rod-receiving heads of said pedicle screws;
    affixing a marking collar to said template rod adjacent one of said pedicle screws;
    withdrawing said template rod and said guide wire medial portion;
    utilizing said marking collar of said template rod to determine the proper length of said fixation rod, and cutting said fixation rod.

11. The method of claim 1, further comprising the steps of:
    grasping the ends of said fixation rod after said fixation rod has been positioned in said rod-receiving heads of said pedicle screws; and
    manipulating the position of one or more of said pedicle screws by moving said fixation rod.

12. The method of claim 1, further comprising the steps of:
    coaxially mounting a compression tool on said fixation rod after said fixation rod has been positioned in one of said rod-receiving heads of said pedicle screws;
    advancing said compression tool against pedicle screw while retaining said fixation rod in order to alter the position of said pedicle screw relative to said fixation rod;
    securing said pedicle screw to said fixation rod; and
    removing said compression tool.

* * * * *